United States Patent [19]

Collen et al.

[11] Patent Number: 4,752,603
[45] Date of Patent: Jun. 21, 1988

[54] PLASMINOGEN ACTIVATOR AND PHARMACEUTICAL COMPOSITION HAVING THROMBOLYTIC ACTIVITY

[75] Inventors: Desire J. Collen, Leuven, Belgium; Dingeman C. Rijken, Leiden, Netherlands; Osamu Matsuo, Osaka, Japan

[73] Assignee: Leuven Research and Development VZW, Leuven Belgium

[21] Appl. No.: 867,561

[22] Filed: May 28, 1986

Related U.S. Application Data

[63] Continuation of Ser. No. 640,550, Aug. 15, 1984, abandoned, which is a continuation of Ser. No. 272,093, Jun. 10, 1981, abandoned, which is a continuation-in-part of Ser. No. 183,638, Sep. 3, 1980, abandoned.

[30] Foreign Application Priority Data

Jun. 11, 1980 [NL] Netherlands ................. 8003402

[51] Int. Cl.$^4$ .......................................... A61K 37/00
[52] U.S. Cl. ........................................ 514/21; 514/2; 514/8; 530/300; 530/350; 530/828
[58] Field of Search ................. 514/2, 21, 8; 530/828, 530/300, 350

[56] References Cited

U.S. PATENT DOCUMENTS 3,904,480  9/1975  Hull et al. .
4,245,051  1/1981  Reich et al. .
4,259,447  4/1981  Hafeli .
4,317,882  4/1982  Horiguchi et al. .
4,370,417  1/1983  Hung et al. .

FOREIGN PATENT DOCUMENTS 0005644  11/1979  European Pat. Off. .
1492959  11/1977  United Kingdom .
1551275   8/1979  United Kingdom .
2025977   1/1980  United Kingdom .

OTHER PUBLICATIONS

Allen, *Cell. Biol.* 4, 803, (1980); *Chemical Abstracts* 93, No. 183281.
Angles-Cano et al., *C.R. Hebd. Seances Acad. Sc.* 289, 485 (1979); *Chemical Abstracts* 92, No. 3674m (1980).
Aoki, *Journal Biochem.* 75, 731 (1974).
Astrup et al., *Arch. Biochem. Biophys.* 40, 346 (1952).
Barlow et al., *Proc. Serono Symp.* 9, 75 (1977); *Chemical Abstracts* 89, No. 57188j (1978).
Binder et al., *Journal of Biological Chemistry* 254, 1998 (1979).
Camiolo et al., *PSEBM* 138, 277 (1971).
Christman et al., *Proteinases in Mammalian Cells and Tissues,* (A. J. Barrett, ed.; Elsvier, Amsterdam), pp. 91-149.
Collen, *Edward Kowalski Memorial Lecture, Thromb Haem* 43, 77 (1980).
Danoe et al., *Biochemica et Biophysica Acta* 613, 542 (1980); *Chemical Abstracts* 93, No. 90924b (1980).
Danoe et al., *J. Exp. Med.* 147, 745 (1978); *Chemical Abstracts* 88, No. 150159q (1978).
Fraki et al., *J. Cutaneous Pathol.* 6, 195 (1979); *Chemical Abstracts* 92, No. 445w (1980).
Granelli-Piperino et al., *J. Exp. Medicine* 148, 223 (1978).
Heussen et al., *Analytical Biochemistry* 102, 196 (1980); *Chemical Abstracts* 92, No. 89750q.
Klavina et al., *Produtsenty Aminokisolot i Fermentov* 1978, 94; *Chemical Abstracts* 89, No. 125054q (1978).
Ouchterlony, *Progress in Allergy V,* (P. Kallos, ed.), 1 (1958).
Petrenko, *Purification and Properties of Plasminogen Activator from Human Blood Plasma after Sudden Death,* p. 1127; *Biokhimiya* 43, 1438 (1978); *Chemcial Abstracts* 89, No. 192926p (1978).
Porath et al., *Nature* 258, 598 (1975).
Pye et al., *Proc. Serono Symp.* 9, 43 (1977); *Chemical Abstracts* 89, No. 159241p (1978).
Radcliffe et al., *Archives of Biochemistry and Biophysics* 189, 185 (1978).
Rijken et al., *Biochemica et Biophysica Acta* 580, 140 (1979); *Chemical Abstracts* 91, No. 170680t (1979).
Rijken, D. C., *Plasminogen Activator from Human Tissue,* Thesis pp. 1-125 (1980).
Rijken, D. C. et al., *J. Biol. Chem.* 256, 7035 (1981).
Roblin et al., *Cancer Research* 40, 2706 (1980); *Chemical Abstracts* 93, No. 126098b (1980).
Thorsen et al., *Thrombos Diathes. haemorh* 28, 65 (1972).
Thorsen, *Danish Medical Bulletin* 24, 189 (1977).
Shiba et al., JA 7844612, 21 Apr. 1978; *Chemical Abstracts* 89, No. 103261c (1978).
Vetterlein et al., *J. Biol. Chem.* 254, 575 (9179); *Chemical Abstracts* 90, No. 135631k (1979).
Vermylen et al., *Clin. Chim. Acta* 8, 418 (1963).
Wallen, *Progress in Chemical Fibrinolysis and Thrombolysis,* 3, 167.
Wang et al., *Cancer Research* 40, 288 (1980); *Chemical Abstracts* 92, No. 92449d.
Weber & Osborn, *J. Biol. Chem.* 244, 4406 (1969).
Wilson, E. L. et al., *Chemical Abstracts* 92, No. 144679a (1980).
Wu et al., *Int. J. Biochem.* 10, 1001 (1979); *Chemical Abstracts* 92, No. 54020z (1980).
Sumitomo Chemical Co., Jap. Kokai 79147993, 19 Nov. 1979; *Chemical Abstracts* 92, No. 106531p (1980).
*Chemical Abstract Ninth Collection Index,* 70-85, 29549cs (1972-1976).
Wiman et al., *Nature* 272, 549 (1978).

*Primary Examiner*—Sam Rosen
*Attorney, Agent, or Firm*—Walter H. Dreger

[57] ABSTRACT

A new plasminogen activator which is very similar to the plasminogen activator from blood can be isolated in good amounts from the culture fluid of human melanoma cells.

This new plasminogen activator has a strong thrombolytic effect and pharmaceutical compositions thereof may be used in the therapeutic treatment of thrombosis disorders.

3 Claims, No Drawings

PLASMINOGEN ACTIVATOR AND PHARMACEUTICAL COMPOSITION HAVING THROMBOLYTIC ACTIVITY

This application is a continuation of application Ser. No. 640,550, filed Aug. 15, 1984, now abandoned, which in turn is a continuation of application Ser. No. 272,093, filed June 10, 1981, now abandoned, which in turn is a continuation-in-part of application Ser. No. 183,638, filed Sept. 3, 1980, now abandoned.

This invention relates to a new plasminogen activator isolated from cell cultures and capable of being prepared at a relatively large scale. Moreover, it relates to a method of purifying and isolating this activator, and further to a thrombolytically active pharmaceutical composition which contains such a plasminogen activator and which can be used in the therepeutic treatment of coagulation disorders, in particular of thromboembolic diseases.

It is well known that surgery, delivery, major trauma and infectious diseases are associated with an increased risk of thrombosis, i.e. formation of intravascular blood clots. One may endeavor to prevent such clots by administering anticoagulants, such as heparin, coumarin derivatives, snake venom components or indanediol. In the case where thrombosis has occurred, however, use may be made of thrombolytic agents whose function is to move the resulting blood clots from the blood vessels by dissolution (lysis).

For a better understanding of the present invention it is noted that blood clots are composed of fibrin which has been formed from fibrinogen under action of the enzyme thrombin. Normal blood contains plasminogen which after activation to plasmin is capable of dissolving fibrin and splitting it enzymatically. A plasminogen activator is naturally present in normal blood or is released into the blood so that the circulating blood contains in principle all ingredients necessary to degrade and remove an intravascular blood clot once it has been formed. In reality, however, it appears that the thrombolytic potential of the body is frequently insufficient for this purpose which may be owing at least partly to an insufficient concentration of plasminogen activator in blood. This means that an adequate removal of intravascular thrombi may require the use of exogenously administered thrombolytic agents.

Until today, mainly urokinase, a plasminogen activator isolated from urine or from cultured kidney cells, and streptokinase, a plasminogen activator from streptococci have been used as thrombolytic agents. Both agents may be prepared on a relatively large scale and are frequently used presently. However, since urokinase and streptokinase are different from the normal plasminogen activator from blood and since they have no specific affinity for fibrin, the results of urokinase and streptokinase in the treatment of thrombosis are not satisfactory in all respects. Relatively large doses of these agents are needed to produce the desired effect and this is associated with a high risk of side effects such as fibrinogenolysis and internal bleedings. Thus, there is a constant need for thrombolytically active agents and substances which may be produced at a relatively large scale as well and which are more effective in treating thrombosis.

The invention has for its object to provide a plasminogen activator which has a strong relationship to the normal plasminogen activator from blood and which may be produced at a relatively large scale. An additional object is to provide purification methods for such a plasminogen activator. Further, the invention has for its purpose to prepare a thrombolytically active composition which is available at large scale and which is more effective than former compositions in the treatment of thrombosis.

During investigations which formed the basis of the present invention, it has surprisingly been found that a plasminogen activator which is very similar to the plasminogen activator from blood can be isolated in fairly good amounts from the culture fluid of human melanoma cells. Melanoma cells are pigmented tumor cells which may be cultivated continuously in the form of cell cultures and thereby secrete a relatively large proportion of plasminogen activator. This provides an opportunity for preparing the plasminogen activator secreted by the cells at a relatively large scale. The resulting activator appears to be strongly related to the blood activator in several respects but is less strongly related to the known substances like urokinase and streptokinase. This offers good prospects for its utilization in pharmaceutical compositions. A strong thrombolytic effect has been found indeed during experiments with the new activator and it has appeared that smaller doses than the urokinase are sufficient and that side effects are substantially absent. As a consequence thereof, compositions containing the new activator may be utilized with good results in the therapeutic treatment of thrombosis disorders.

Therefore, the invention provides in the first place a plasminogen activator from human melanoma cells. Further, it provides a thrombolytically active pharmaceutical composition which contains an effective amount of this plasminogen activator. Moreover, the invention provides methods for the preparation and purification of the activator, a method for preparing the composition and a method for the therapeutic treatment of thrombosis disorders with the aid of the new composition.

It is known that several types of tumor cells will secrete a plasminogen activator during cultivation in cell culture (Christman et al in: Proteinases in Mammalian Cells and Tissues (ed. A. J. Barrett) pp 91-149, Elsevier, Amsterdam) but most of these plasminogen activators are related to urokinase (compare Vetterlein et al, J. Biol. Chem. 254, 575-578 (1979)), and moreover, none of them has ever been isolated in sufficient amount. Therefore, it was surprising that human melanoma cells in cell culture secrete a plasminogen activator which is closely related to the activator circulating in blood, and moreover in such amounts that the activator may be recovered and purified from them on a fair scale.

The plasminogen activator according to the invention may be prepared by cultivating human melanoma cells in a suitable growth medium, followed by recovery of the culture fluid containing the activator, and purification of the resulting fluid.

Purification of the resulting culture fluid may be effected in principle in any suitable way and may include each separation method which is usual in protein chemistry, such as fractionated precipitation with for example salts, organic solvents or polyethylene glycols, electrophoresis using different buffers and carriers, gel filtration on for instance crosslinked dextrans, crosslinked or noncrosslinked agarose. Crosslinked poly acrylamide, or mixtures thereof, and other chromatographic operations based on partition or adsorption/desorption. The latter operations may be performed batch-wise or in columns. Partition chromatography or absorption/desorption chromatography may be effected for example by ion exchange, hydrophobic interaction, ligand exchange or biospecific affinity. In these methods, the same media as for gel filtration may be used as a stationary phase, but with suitable groups attached to the inner or outer surface of the particles. Aqueous buffers which may contain several additives such as inorganic or organic salts, organic solvents, surface active substances and/or substances which interfere with one of more components of the separation system, may be used as the mobile phase.

In a preferred embodiment, ligand exchange chromatography is used preferably with a metal chelate agarose as the stationary phase. For instance, the fluid to be purified is passed over a column of zinc chelate agarose at a pH of 7.5, whereupon the adsorbed plasminogen activator may be eluted with an imidazole-containing buffer solution. The zinc chelate agarose may be prepared by coupling iminodiacetic acid to agarose and saturating the product with zinc chloride utilization of a column will give better results than a batch-wise method.

In another preferred embodiment, in addition to or instead of the foregoing embodiment, affinity chromatography is used, preferably with the aid of lectin agarose as a stationary phase. For instance, the fluid to be purified is passed over a column of lectin agarose at a pH of 7.5 whereupon the adsorbed plasminogen activator is eluted at the same pH with a buffer solution containing α-D-methylmannoside and potassium thiocyanate.

A third preferred embodiment, mainly used us a last stage, is formed by gel filtration, preferably on cross-linked dextran particles.

In these purification methods, it is advisable to add a surfactant or detergent to all buffer solutions as used in order to prevent a strong tendency of the plasminogen activator to adsorb to glass ware surfaces, and to improve stability of the product. Good results have been obtained with non-ionic detergents in final concentrations of 0.01% (vol/vol) or even 0.001% (vol/vol). These non-ionic detergents will mainly comprise polyglycolethers of fatty alcohols, polyglycolethers of alkylphenols or polyglycolesters of fatty acids.

Further, it may be advisable to perform these purification methods, as well as the initial cultivation of the melanoma cells, in the presence of aprotinin in order to prevent degradation of the plasminogen activator molecule during such procedures. Aprotinin is a high-molecular weight trypsin inhibitor isolated from bovine pancreas tissue. It appears to have influence on the molecular weight of the plasminogen activator, as shown below.

A good purification and a clear increase of specific activity may be achieved by utilization of the purification methods as described, and the purified product will be suitable for identification tests and for conversion to a pharmaceutical composition.

The resulting plasminogen activator from melanoma cells appears to have a molecular weight of about 72,000 in unreduced form, when determined with SDS-polyacrylamide gel electrophoresis. In reduced form, it may show two bands having molecular weights of about 33,000 and about 39,000 respectively if cultivation and purification were performed in the absence of aprotinin, or else one band having a molecular weight of about 72,000 if cultivation and purification were performed in the presence of aprotinin. The first product seems to be a proteolytic degradation product, while the latter is a natural product. Thus, it seems that aprotinin prevents degradation of the activator molecule.

The aminoacid compositions of activators produced in the absence and presence of aprotinin are given in tables 1 and 3 respectively and show a great similarity. Further, the resulting plasminogen activator appears to bind strongly to fibrin.

As a result of all these properties, it may be stated that the new plasminogen activator is very similar to the normal plasminogen activator from human blood.

In immunological respect, the new activator shows differences with urokinase.

During experiments with blood clots generated in vitro, the plasminogen activator from melanoma cells appears to have a higher fibrinolytic and thrombolytic effect than urokinase and moreover a lower fibrinogenolytic side effect. This indicates that the new plasminogen activator is better suitable than urokinase for utilization as a thrombolytic composition.

A galenic composition may be made from the purified plasminogen activator in a conventional way, with or without the use of additives such as sodium chloride, glucose, mannitol, albumin, and the like. The composition will mostly be suitable for parenteral administration, including intravenous or intraarterial injection or infusion.

The resulting composition may be administered to patients in a suitable dose and will have a potent and effective thrombolytic effect with little or no side effects. Therefore, the composition may be used for curing acute and chronic thromboembolic occlusions of different vascular beds such as encountered in deep vein thrombosis, pulmonary embolism, myocardial infarction, arterial occlusion, extracorporeal circulation and arteriovenous shunts.

The invention is further illustrated by the following examples which include tests for characterization of the new activator.

EXAMPLE 1

Cultivation and recovery

A human melanoma cell line (patient Bo.) was obtained from Dr. D. B. Rifkin, Rockefeller University, New York, N.Y., USA. The growth medium used for this cell line was modified Eagle's essential medium (Flow Laboratories, UK), supplemented with sodium bicarbonate (16 ml 6.5% solution per liter of medium), L-glutamine (10 ml 200 mN solution per liter of medium) and heat-inactivated newborn calf serum (Gibco, Paisley, U.K.) (final concentration 10%).

The melanoma cells were grown to confluent monolayers in the above growth medium. Then they were washed with growth medium without calf serum and incubated for three days in the same serum-free growth medium. After each day the culture fluid was collected and replaced, centrifuged at 7000xg for 20 minutes and stored at −20° C. until use. The combined culture fluids had a protein content of about 180 μg/ml and a plasminogen activator activity of about 60 IU/ml (or about 330 IU/mg).

Protein content of the fluids in this and other examples was determined by light absorption at 280 nm.

Plasminogen activator activity was determined on plasminogen-containing bovine fibrin plates according to Astrup et al, Arch. Biochem. Biophys. 40, 346–351 (1952) and expressed in international units (IU), thereby using the WHO 1st international Reference Preparation of Urokinase (66/46) as a standard. The same method of assay was used in all other examples.

EXAMPLE 2

Purification

The combined culture fluids of example 1 were subjected to a three-step purification procedure. All steps thereof were performed at 4° C. To the buffer solution used in these steps, a small amount of Tween 80, a nonionic detergent of J. T. Baker Chemicals, was added in order to prevent adsorption of the plasminogen activator to glass-ware.

(a) In a first step, the combined culture fluids were subjected to chromatography on zinc chelate agarose. This material was prepared by coupling iminodiacetic acid to agarose particles (Sepharose 4B of Pharmacia Fine Chemicals, Uppsala, Sweden) and by saturating the product with zinc chloride. The coupling method has been disclosed by Porath et al, Nature, 258, 598–599 (1975). After use, the zinc chelate agarose could be regenerated by washing consecutively with 0.05M ethylene diamine tetraacetic acid (EDTA) of pH=8.0, 0.05M $NH_4HCO_3$ of pH=10.5, and water, and by resaturating it with zinc chloride.

A column of zinc chelate agarose (5×10 cm) was equilibrated with 0.02M Tris HCl buffer solution of pH=7.5, containing 1M NaCl and 0.01% (v/v) of Tween 80. In this buffer solution, Tris is trihydroxymethylaminomethane. Ten liters of combined culture fluids were applied to the equilibrated zinc chelate agarose column. The flow rate was 200 ml/h. The column was washed with equilibration buffer and then eluted with the same buffer (total volume 1 liter) containing a linear gradient (from 0 to 0.05M) of imidazole. Fractions of 10 ml were collected at a flow rate of 120 ml/h and all fractions were assayed on plasminogen activator activity and protein concentration (see above). This showed that plasminogen activator was desorbed as a single peak in fractions 28–42, only partly separated from a big protein peak. The activator-containing fractions were pooled (151 ml). They had a protein content of 900 $\mu$g/ml and a specific activity of 1100 IU/ml or 3600 IU/mg. Thus, the total yield was 83% and the purification factor was 11.

(b) In a second step, the plasminogen activator solution resulting from the first step was subjected to chromatography on lectin agarose (Concanavalin A Sepharose from Pharmacia Fine Chemicals, Uppala, Sweden).

A column of Concanavalin A agarose (0.9×25 cm) was equilibrated with 0.01M phosphate buffer of pH=7.5, containing 1M NaCl and 0.01% (v/v) of Tween 80. The pooled activator-containing fractions of step (a) were applied to this column. Fractions of 4 ml were collected at a flow rate of 8 ml/h. The column was washed with equilibration buffer and eluted with the same buffer (total volume 200 ml) containing linear gradients of $\alpha$-D-methylmannoside (from 0 to 0.6M) and potassium thiocyanate (from 0 to 2M). Fractions of 4 ml were again collected and assayed each on plasminogen activator activity and protein concentration. It appeared that the plasminogen activator was desorbed at about 0.3M $\alpha$-D-methylmannoside and 1M potassium thiocyanate. The activator was recovered in a single peak separated from a clear protein peak. The activator peak containing fractions were pooled (84 ml). They had a protein content of 159 $\mu$g/ml and specific activity of 1300 IU/ml or about 25,000 IU/mg. Thus, the overall yield was 56% and the overall purification factor was 77.

(c) In a third step, the plasminogen activator solution resulting from the second step was subjected to gel filtration on crosslinked dextran particles. The material used was Sephadex G-150 (superfine) from Pharmacia Fine Chemicals, Uppsala, Sweden. Prior to gel filtration, solid potassium thiocynate was added to the plasminogen activator solution to reach a final concentration of 1.6M and the solution was concentrated to about 10 ml by dialysis against solid polyethylene glycol 20,000. A small precipitate was removed by centrifugation at 10,000 xg for 15 minutes.

A Sephadex G-150 (superfine) column (2.5×90 cm) was equilibrated with 0.01M phosphate buffer of pH=7.5, containing 1.6M potassium thiocyanate and 0.01% (v/v) of Tween 80. Then, the concentrated activator solution was applied to the column and filtered therethrough, followed by the equilibration buffer. Fractions of 3.4 ml were collected at a flow rate of 6.8 ml/h and assayed for plasminogen activator activity and protein concentration. It appeared that the plasminogen activator emerged from the column as a single peak which coincided with a protein peak. The activator-containing fractions were pooled (37 ml). They had a protein content of 81 $\mu$g/ml and a specific activity of 7200 IU/ml, or about 90,000 IU/mg using the WHO First International Reference Preparation of urokinase as standard, which corresponds, and is equivalent, to about 500,000 IU/mg. when assayed using the WHO First International Reference Preparation of t-PA [(tissue) plasminogen activator] as standard. Gaffney and Curtiss, "A Collaborative Study of a Proposed International Standard for Tissue Plasminogen Activator (t-PA)," Thromb. Haemost. 53, 134 (1985). See also Holovet, Boes and Collen, Blood 69, 284 (1987). Thus, the total yield was 46% and the purification factor as compared with the starting material was 263.

The resulting activator solution was stored at −20° C. and used for characterization and utilization experiments.

EXAMPLE 3

Characterization

The purified plasminogen activator solution resulting from example 2 was subjected to several characterization tests.

(a) When subjected to SDS-polyacrylamide gel electrophoresis, the new activator showed one band with an estimated molecular weight of 72,000. After reduction with dithiothreitol, two bands were observed with molecular weights of about 33,000 and about 39,000, respectively.

In this test, SDS-acrylamide gel electrophoresis was performed according to Weber and Osborn, J. Biol. Chem. 244, 4406–4412 (1969), using 7% gels. The molecular weight was estimated by means of a calibration kit (Pharmacia Fine Chemicals, Uppsala, Sweden) which contained phosphorylase b (94,000), serum albumin (67,000), ovalbumin (43,000), carbonic anhydrase (30,000), trypsin inhibitor (20,000) and $\alpha_2$-lactalbumin (14,400).

(b) When subjected to hydrolysis with 6M HCl in vacuo at 110° C. for 20 hours, followed by amino acid determination, the new activator showed the following amino acid composition (in percent of total);

TABLE 1

| Amino acid | Content |
| --- | --- |
| Aspartic acid | 10.1 |
| Threonine | 5.0 |
| Serine | 11.4 |
| Glutamic acid | 11.5 |
| Proline | 5.7 |
| Glycine | 11.2 |
| Alanine | 7.8 |
| Cysteine | N.D. |
| Valine | 4.4 |
| Methionine | 1.5 |
| Isoleucine | 3.1 |
| Leucine | 7.6 |
| Tyrosine | 4.1 |
| Phenylalanine | 3.3 |
| Lysine | 4.6 |
| Histidine | 3.3 |
| Arginine | 5.6 |
| Tryptophan | N.D. |

N.D. = Not Determined.

(c) When subjected to a fibrin binding test, it appeared that the new activator was bound to fibrin, in contrast to urokinase which dod not bind at all.

The test was effected by adding fibrinogen and thrombin to the activator solution. After incubation at 37° C. for 30 min, fibrin was removed by centrifugation, washed and extracted with potassium thiocyanate (1.6M). The results are summarized in Table 2.

TABLE 2

|  | New activator (%) | Urokinase (%) |
| --- | --- | --- |
| Unbound | 10 ± 1 | 98 ± 1 |
| KSCN extract | 61 ± 3 | 8 ± 2 |

(d) When subjected to immunodiffusion analysis, the new activator appeared to be immunologically different from human urokinase (Mr=54,000) since precipitin lines developed between the new activator and antibodies against the activator, while such precipitin lines were absent between urokinase and the same activator antibodies. This immunodiffusion analysis was performed by the method of Ouchterlony, Progress in Allergy, Vol.V (Kallos, P.ed.) pages 1 et sed, Karger, Basel/New York, 1958. Tween 80 was added to the agarose to reach a final concentration of 0.1% (v/v).

(e) When subjected to quenching experiments on a plasminogen-containing bovine fibrin plate, similar results were obtained. The fibrinolytic activities of the new plasminogen activator were quenched completely by antibodies (IgG fraction) against that activator but the fibrinolytic activities of urokinase solution (having the same activity) were not quenched thereby. Further, the IgG fraction of a control antiserum did not quench any fibrinolytic activity in the concentration range of the experiments.

The quenching experiments were performed according to Astrup et al, Arch. Biochem. Biophys., 40, 346-351 (1951). The plasminogen activator (140 IU/ml) was dissolved in 0.02M Tris/CHl of pH 7.5, containing 0.15M NaCl and 0.01% of Tween 80.

The antibodies needed for tests (d) and (e) were prepared as follows: an antiserum against the new plasminogen activator was raised in a rabbit by injecting 100 μg of purified activator, dissolved in 0.5 ml of physiological saline solution and emulsified with 0.5 ml of Freund's Complete Adjuvant. Booster injections of 50 μg were given at two-week intervals. Serum was collected one week after the second booster. The IgG fraction of the antiserum was isolated by affinity chromatography on Protein A Sepharose and dialysed against 0.15M NaCl solution.

EXAMPLE 4

Procedure in the presence of aprotinin

Melanoma cells were cultivated according to the procedure of example 1, with the exception that aprotinin (Bayer, Leverkusen, FRG) was added both to the serum-containing and serum-free growth medium (final concentration 20 KIU/ml, i.e. 20 Kallikrein Inhibitor Units per ml).

After incubation for three consecutive days with collection and replacement of culture fluid at the end of each day, the combined culture fluids had a protein content of about 180 μg/ml and a plasminogen activator of about 60 IU/ml (or about 330 IU/mg).

Protein content of the fluids and plasminogen activator activity were determined in the same way as in the preceding examples but an appropriate amount of aprotinin (in this case until a final concentration of 20 KIU/ml) was added to the urokinase solution used as a standard in the Astrup et al method since it appeared that aprotinin as present in the plasminogen activator solution reduced the response on the fibrin plates.

The combined culture fluids were subjected to a three-step purification procedure in the same way as in example 2, with the exception that aprotinin was added to the buffers of the first and second purification step (final concentration 10 IUK/ml). This aprotnin was omitted during the third step in order to obtain a final product without aprotinin. The presence of aprotinin did not influence the chromatographic behavior nor the yield and specific activity of the plasminogen activator and this meant that similar results as in example 2 were obtained.

The purified plasminogen activator solution was subjected to several characterization tests as in example 3.

When subjected to SDS-polyacrylamide gel electrophoresis, the activator showed one band with an estimated molecular weight of 72,000. After reduction with dithiothreitol, again one band having an estimated molecular weight of about 72,000 was observed. This is indicative of a natural undegraded product whereas the product tested in example 3 may be a proteolytic degradation product.

When subjected to hydrolysis with 6M HCl in vacuo at 110° C. for 20 hours, followed by amino acid determination, the activator of this example showed the following amino composition (in percent of total):

TABLE 3

| Amino acid | Content |
| --- | --- |
| Aspartic acid | 9.8 |
| Threonine | 5.4 |
| Serine | 9.2 |
| Glutamic acid | 13.1 |
| Proline | 7.1 |
| Glycine | 10.4 |
| Alanine | 6.6 |
| Cysteine | N.D. |
| Valine | 4.1 |
| Methionine | 0.9 |
| Isoleucine | 3.0 |
| Leucine | 8.1 |

TABLE 3-continued

| Amino acid | Content |
| --- | --- |
| Tyrosine | 4.0 |
| Phenylalanine | 3.7 |
| Histidine | 3.3 |
| Lysine | 5.5 |
| Arginine | 5.9 |
| Tryptophan | N.D. |

N.D. = Not Determined.

Further, the activator of this example appeared to have sufficient binding capacity to fibrin, and behaved in the same way as the product of example 2 when subjected to immunodiffusion analysis and quenching experiments.

EXAMPLE 5

Fibrinolytic, fibrinogenolytic and thrombolytic effects.

The relative fibrinolytic effects of the new plasminogen activator and urokinase were compared in a clot lysis system composed of fresh frozen blood bank plasma. In duplicate test tubes, 0.4 ml of plasma was combined and mixed with 50 $\mu$l of activator solution (final concentration ranging from 10 to 200 IU per ml) and 50 ml of human thrombin (final concentration 1 NIH unit per ml) (NIH means National Institute of Health, Bethesda, Md., USA). The activator was the new plasminogen activator in one series resulting from example 2, and urokinase in another series of experiments. After clot formation, the mixtures were incubated at 37° C. and the time required for complete clot lysis was recorded.

In this system, a clot of fibrin is formed by the action of added thrombin on plasma fibrinogen, and lysis of the clot may be effected by the added activator which causes transformation of plasma plasminogen to plasmin. This clot lysis may be antagonized by the presence of antiplasmin in the blood plasma.

It appeared that both activators caused lysis of the clot and thus had a fibrinolytic effect, but the nature of these effects was different. At high activator concentrations, the lysis times were comparable, but at low concentrations the new plasminogen activator was far more effective than urokinase. At a urokinase concentration of 80 units per ml, the plasma clot did not lyse in 24 hours whereas the lysis time induced with 20 units of the new plasminogen activator was less than 2 hours.

(b) The fibrigenolytic effects of the new plasminogen activator and urokinase were compared in plasma systems. To 1.8 ml of human plasma, 0.2 ml of activator solution (final concentration ranging from 5 to 200 IU/ml) were added. At different time intervals, 0.2 ml samples were taken for determination of their fibrinogen level by the method of Vermylen et al, Clin. Chim. Acta, 8, 418–424, (1963).

It appeared that there was a difference in behavior between urokinase and the new activator. At 100 units per ml, a mild degree of fibrinogen breakdown was observed with urokinase but not with the new plasminogen activator.

(c) The thrombolytic effects of the new plasminogen activator and of urokinase were measured in an artificial system comprising a radioactive human thrombus suspended in an amount of circulating blood plasma in which an activator solution was slowly infused. Plasma samples were taken before the start of the activator infusion and at hourly intervals for 8–12 hours. The degree of thrombolysis was estimated from the released radioactivity and expressed as percent.

It appeared that significant thrombolysis in 12 hours could be obtained with 10 units or more of the new plasminogen activator per ml of plasma, but not with 20 units of urokinase per ml. The specific thrombolytic effect of the new activator in this system is about 10 times higher than that of urokinase. Furthermore, it appears that after the end of the activator infusion the rate of thrombolysis by urokinase tends to level off whereas thrombolysis induced by the new plasminogen activator is much more progressive.

EXAMPLE 6

Pharmaceutical composition

A solution of the new activator in a phosphate buffered physiological saline solution which contains 0.001% of Tween 80 and 0.01–1% of albumin or mannitol, may be used as a composition for intravenous injection.

We claim:

1. Human plasminogen activator, having thrombolytic properties, immunologically distinct from urokinase and having a specific activity of about 500,000 IU/mg. using the WHO First International Reference Preparation of t-PA (tissue plasminogen activator) as assay standard or a specific activity of about 90,000 IU/mg. using the WHO First International Reference Preparation of urokinase as assay standard.

2. A pharmaceutically acceptable composition having thrombolytic activity comprising a thrombolytically effective amount of human plasminogen activator according to claim 1 and a pharmaceutically acceptable carrier or diluent.

3. A method for therapeutic treatment of thrombosis disorders comprising administering to a patient a thrombolytically effective amount of human plasminogen activator as defined in claim 1 or a composition as defined in claim 2.

* * * * *

UNITED STATES PATENT AND TRADEMARK OFFICE
CERTIFICATE OF CORRECTION

PATENT NO. : 4,752,603
DATED : 21 June 1988
INVENTOR(S) : Desire J. Collen et al.

It is certified that error appears in the above-identified patent and that said Letters Patent is hereby corrected as shown below:

On the cover page, left column, about line 46, change "3674m" to --36746m--.

On the cover page, right column, about line 13, change "Chemcial" to --Chemical--.

On the cover page, right column, about line 31, change "(9179)" to --(1979)--.

On the cover page, right column, about line 39, between "Wilson, E.L. et al.," and "Chemical", insert --Cancer Research 40, 933 (1980);--.

On Col. 1, line 29, change "clots" to --clot--.

On Col. 2, line 67, change "agarose. Crosslinked" to --agarose, crosslinked--.

On Col. 3, line 16, insert --,-- after "used".

On Col. 3, line 23, change "chloride utilization" to --chloride. Utilization--.

On Col. 3, line 35, change "us" to --as--.

On Col. 3, line 67, insert --,-- after "39,000".

UNITED STATES PATENT AND TRADEMARK OFFICE
CERTIFICATE OF CORRECTION

PATENT NO. : 4,752,603

DATED : June 21, 1988

INVENTOR(S) : Desire J. Collen et al

Page 2 of 2

It is certified that error appears in the above-identified patent and that said Letters Patent is hereby corrected as shown below:

On Col. 5, line 53, change "Uppala" to --Uppsala--.

On Col. 7, line 47, change "sed," to --seq.,--.

On Col. 7, line 62, change "(1951)" to --(1952)--.

On Col. 8, line 28, change "et al" to --et al.--.

Signed and Sealed this

Tenth Day of October, 1989

Attest:

*Attesting Officer*

DONALD J. QUIGG

*Commissioner of Patents and Trademarks*